US010036715B2

(12) United States Patent
Broga et al.

(10) Patent No.: US 10,036,715 B2
(45) Date of Patent: *Jul. 31, 2018

(54) AUTOMATIC ISOTHERMAL TITRATION MICROCALORIMETER APPARATUS AND METHOD OF USE

(71) Applicant: Malvern Instruments Incorporated, Westborough, MA (US)

(72) Inventors: Martin Broga, Amherst, MA (US); Phillip Price, North Granby, CT (US); Stephen Smith, Northampton, MA (US)

(73) Assignee: Malvern Panalytical Inc., Westborough, MA (US)

( * ) Notice: Subject to any disclaimer, the term of this patent is extended or adjusted under 35 U.S.C. 154(b) by 217 days.

This patent is subject to a terminal disclaimer.

(21) Appl. No.: 15/192,712

(22) Filed: Jun. 24, 2016

(65) Prior Publication Data
US 2016/0363548 A1 Dec. 15, 2016

Related U.S. Application Data

(63) Continuation of application No. 14/736,905, filed on Jun. 11, 2015, now Pat. No. 9,404,876, which is a
(Continued)

(51) Int. Cl.
*G01N 25/20* (2006.01)
*B01L 3/02* (2006.01)
(Continued)

(52) U.S. Cl.
CPC ............ *G01N 25/4873* (2013.01); *B01L 3/02* (2013.01); *G01N 25/48* (2013.01);
(Continued)

(58) Field of Classification Search
CPC ........ G01K 17/006; G01N 1/14; G01N 25/20; G01N 25/48; G01N 25/4813;
(Continued)

(56) References Cited

U.S. PATENT DOCUMENTS 3,210,996 A 10/1965 Harwood et al.
3,973,696 A 8/1976 Moore
(Continued)

FOREIGN PATENT DOCUMENTS

DE 2910751 10/1980
DE 3242469 5/1984
(Continued)

OTHER PUBLICATIONS

Cooper, A. et al. (1994). "Isothermal Titration Microcalorimetry," located at <http://www.chem.gla.ac.uk/staff/alancMMB-ITC-1 994.pdf> retrieved on Jan. 15, 2010. (14 pages). (Year: 1994).*
(Continued)

*Primary Examiner* — Jennifer Wecker
(74) *Attorney, Agent, or Firm* — Morrison & Foerster LLP

(57) ABSTRACT

Automated isothermal titration micro calorimetry (ITC) system comprising a micro calorimeter with a sample cell and a reference cell, the sample cell is accessible via a sample cell stem and the reference cell is accessible via a reference cell stem. The system further comprises an automatic pipette assembly comprising a syringe with a titration needle arranged to be inserted into the sample cell for supplying titrant, the pipette assembly comprises an activator for driving a plunger in the syringe, a pipette translation unit supporting the pipette assembly and being arranged to place pipette in position for titration, washing and filling operations, a wash station for the titrant needle, and a cell preparation unit arranged to perform operations for replacing the sample liquid in the sample cell when the pipette is placed in another position than the position for titration.

11 Claims, 13 Drawing Sheets

Related U.S. Application Data continuation of application No. 12/326,300, filed on Dec. 2, 2008, now Pat. No. 9,103,782.

(51) Int. Cl.
*G01N 35/00* (2006.01)
*G01N 35/10* (2006.01)
*G01K 17/00* (2006.01)
*G01N 25/48* (2006.01)
*G01N 1/14* (2006.01)

(52) U.S. Cl.
CPC ..... *G01N 25/4866* (2013.01); *G01N 35/0092* (2013.01); *G01N 35/00584* (2013.01); *G01N 35/1002* (2013.01); *G01K 17/006* (2013.01); *G01N 1/14* (2013.01); *G01N 25/20* (2013.01); *G01N 25/4813* (2013.01)

(58) Field of Classification Search
CPC ........... G01N 25/4866; G01N 25/4873; G01N 35/00584; G01N 35/1002
See application file for complete search history.

(56) References Cited

U.S. PATENT DOCUMENTS

| | | |
|---|---|---|
| 4,543,238 A | 9/1985 | Mimura et al. |
| 4,555,957 A | 12/1985 | Frankel et al. |
| 4,604,363 A | 8/1986 | Newhouse et al. |
| 4,713,974 A | 12/1987 | Stone |
| 4,731,225 A | 3/1988 | Wakatake |
| 4,816,730 A | 3/1989 | Wilhelm, Jr. et al. |
| 4,888,998 A | 12/1989 | Buzza et al. |
| 4,923,306 A | 5/1990 | Fauske |
| 4,951,513 A | 8/1990 | Koike |
| 4,957,707 A | 9/1990 | Hofelich et al. |
| 4,981,801 A | 1/1991 | Suzuki et al. |
| 5,079,959 A | 1/1992 | Miyake et al. |
| 5,102,623 A | 4/1992 | Yamamoto et al. |
| 5,104,621 A | 4/1992 | Pfost et al. |
| 5,138,868 A | 8/1992 | Long |
| 5,141,871 A | 8/1992 | Kureshy et al. |
| 5,215,714 A | 6/1993 | Okada et al. |
| 5,305,650 A | 4/1994 | Koike et al. |
| 5,322,360 A | 6/1994 | Willis et al. |
| 5,340,541 A | 8/1994 | Jackson et al. |
| 5,358,691 A | 10/1994 | Clark et al. |
| 5,365,798 A | 11/1994 | Kressirer |
| 5,408,891 A | 4/1995 | Barber et al. |
| 5,443,791 A | 8/1995 | Cathcart et al. |
| 5,474,744 A | 12/1995 | Lerch |
| 5,482,861 A | 1/1996 | Clark et al. |
| 5,544,535 A | 8/1996 | Thomas |
| 5,610,069 A | 3/1997 | Clark et al. |
| 5,756,905 A | 5/1998 | Ueda |
| 5,762,878 A | 6/1998 | Clark et al. |
| 5,807,523 A | 9/1998 | Watts et al. |
| 5,813,763 A | 9/1998 | Plotnikov et al. |
| 5,855,851 A | 1/1999 | Matsubara et al. |
| 5,876,668 A | 3/1999 | Kawashima et al. |
| 5,976,470 A | 11/1999 | Maiefski et al. |
| 6,096,561 A | 8/2000 | Tayi |
| 6,143,252 A | 11/2000 | Haxo, Jr. et al. |
| 6,148,680 A | 11/2000 | Baeuerle et al. |
| 6,193,413 B1 | 2/2001 | Lieberman |
| 6,306,658 B1 | 10/2001 | Turner et al. |
| 6,387,277 B1 | 5/2002 | North, Jr. |
| 6,387,330 B1 | 5/2002 | Bova et al. |
| 6,422,248 B1 | 7/2002 | Fürst et al. |
| 6,423,536 B1 | 7/2002 | Jovanovich et al. |
| 6,464,391 B2 | 10/2002 | Lyon |
| 6,644,136 B1 | 11/2003 | Carney et al. |
| 6,772,650 B2 | 8/2004 | Ohyama et al. |
| 6,776,966 B2 | 8/2004 | Gebrian et al. |
| 6,818,183 B2 | 11/2004 | Hajduk et al. |
| 6,843,357 B2 | 1/2005 | Bybee et al. |
| 6,846,455 B1 | 1/2005 | Carney et al. |
| 6,945,129 B2 | 9/2005 | Escal |
| 6,953,280 B2 | 10/2005 | Fischer et al. |
| 6,991,765 B2 | 1/2006 | Neilson et al. |
| 7,074,364 B2 | 7/2006 | Jähn et al. |
| 7,138,254 B2 | 11/2006 | Jovanovich et al. |
| 7,288,229 B2 | 10/2007 | Turner et al. |
| 7,416,897 B2 | 8/2008 | Bruce et al. |
| 7,439,076 B1 | 10/2008 | Tokiwa et al. |
| 7,488,106 B2 | 2/2009 | Brushwyler |
| 7,578,613 B2 | 8/2009 | Reading |
| 8,057,756 B2 | 11/2011 | Londo et al. |
| 2002/0172629 A1 | 11/2002 | Jähn et al. |
| 2002/0176803 A1 | 11/2002 | Hamel et al. |
| 2003/0032171 A1 | 2/2003 | Gemmell et al. |
| 2003/0047778 A1 | 3/2003 | Nakamura et al. |
| 2003/0127776 A1 | 7/2003 | Carlson et al. |
| 2003/0215361 A1 | 11/2003 | Jang |
| 2003/0226857 A1 | 12/2003 | Bibbo et al. |
| 2003/0233893 A1 | 12/2003 | Bremer et al. |
| 2004/0024542 A1 | 2/2004 | Plotnikov et al. |
| 2004/0063208 A1 | 4/2004 | Chandler, Jr. |
| 2004/0126783 A1 | 7/2004 | Bortolin et al. |
| 2004/0126890 A1 | 7/2004 | Gjerde et al. |
| 2004/0168529 A1 | 9/2004 | Carlson et al. |
| 2004/0219062 A1 | 11/2004 | Platano et al. |
| 2005/0036536 A1 | 2/2005 | Lewis |
| 2005/0037507 A1 | 2/2005 | Gauer |
| 2005/0135455 A1 | 6/2005 | Peeters |
| 2006/0166373 A1 | 7/2006 | Enoki et al. |
| 2006/0257999 A1 | 11/2006 | Chang et al. |
| 2006/0263250 A1 | 11/2006 | Blouin et al. |
| 2006/0283945 A1 | 12/2006 | Excoffier et al. |
| 2007/0039866 A1 | 2/2007 | Schroeder et al. |
| 2007/0122312 A1 | 5/2007 | Chojnacki et al. |
| 2007/0278154 A1 | 12/2007 | Nagaoka et al. |
| 2007/0286254 A1 | 12/2007 | Fon et al. |
| 2008/0166292 A1 | 7/2008 | Levin et al. |
| 2008/0264187 A1 | 10/2008 | Angus et al. |
| 2009/0031826 A1 | 2/2009 | Stirn et al. |
| 2009/0032065 A1 | 2/2009 | Bantz et al. |
| 2009/0046535 A1 | 2/2009 | Carlson et al. |
| 2009/0186374 A1 | 7/2009 | Okun et al. |
| 2010/0238968 A1* | 9/2010 | Plotnikov ............... G01N 1/14 374/33 |

FOREIGN PATENT DOCUMENTS

| | | |
|---|---|---|
| EP | 1 376 138 | 1/2004 |
| GB | 2 071 317 | 9/1981 |
| GB | 2 121 169 | 12/1983 |
| JP | H02-284050 | 11/1990 |
| WO | WO-81/01045 | 4/1981 |
| WO | WO-87/00086 | 1/1987 |
| WO | WO-93/20440 | 10/1993 |
| WO | WO-95/08774 | 3/1995 |
| WO | WO-2008/018904 | 2/2008 |
| WO | WO-2009/059110 | 5/2009 |

OTHER PUBLICATIONS

Photo of Injection Needle with Stirrer; 1 page.
Photo of Micorcal Omega Device; 1 page.
Photo of PEAQ Auto Fill Port and Injector at Injector Wash and Load Station; 1 page.
Photo of PEAQ Auto Syringe Pumps; 1 page.
Photo of VP Auto ITC I Injection Stirring Insert; 1 page.
Photo of Close-Up of Injection Needle and Stirrer; 1 page.
Photo of PEAQ Auto Rotational Arms; 1 page.
Photo of Auto ITC System; 1 page.
Photo of FPA and Fill Port Engagement Timing for Injector Loading; 1 page.
Photo of iTC200 with Background; 1 page.
Photo of Omega with Keithly; 1 page.
Photo of Syringe Pump Close-UP; 1 page.
Diagram of Auto ITC Plumbing; 1 page.

(56) References Cited

OTHER PUBLICATIONS

Diagram of Auto ITC; 1 page.
MicroCal, LLC., "*Auto ITC Microcalorimeter Preliminary Specifications,*" SMA-0007 Rev H.; 1 page.
Instructions; "*Setup of AutoITC Instrument Only,*" 4 pages.
Wiseman et al. (1989), "*Rapid Measurement of Binding Constants and Heats of Binding Using a New Titration Calorimeter,*" Analytical Biochemistry 179: 131-137.
MicroCal Product Brochure (1998), "*Unexcelled sensitivity Plus most powerful data handling capabilities . . . the New MicroCal MC-2 Scanning Calorimeter*"; 7 pages.
History of MicroCal Instruments (2014) located at www.malvern.com; 1 page.
Peters, William B. et al. (2008), "*Recent Developments in Isothermal Titration Calorimetry*", 31 pages.
MicroCal, LLC., "*AutoITC User's Manual,*" Ultrasensitive Calorimetry for the Life Science, MAU130060 Rev. A; 106 pages.
Plotnikov, K., "*A New Automated Isothermal Titration Calorimetry System for Increased Throughput*"; MicroCal 1 page.
Brandts, Michael J. "*ITC-Derived Binding Constants Using Microgram Quantities of Protein,*" MicroCal, 45 pages.
MicroCal, LLC, Brochure "AutoITC HT Microcalorimeter—Binding & Kinetics;" 2 pages.
MicroCal, LLC., "*AutoITC Experimental Guide,*" Ultrasensitive Calorimetry for the Life Science, MAU230010 Rev. C-2; 29 pages.
MicroCal, LLC., "*AutoITC User's Manual,*" Ultrasensitive Calorimetry for the Life Science, MAU230020 Rev. D; 109 pages.
MicroCal, LLC, "Experimental Guide for AutoITC User's Manual," *Ultrasensitive Calorimetry for the Life Science*, MAU230010 Rev. C-2; 29 pages.
MicroCal, LLC, "AutoITC User's Manual," *Ultrasensitive Calorimetry for the Life Science*, MAU230020 Rev. D; 109 pages.
Supplementary European Search Report dated May 20, 2016, directed to European Application No. 08843953.4; 7 pages.
Jones, Christopher et al. (1994) "Microscopy, Optical Spectroscopy, and Macroscopic Techniques" Chapter 11 in Methods *In Molecular Biology* • 22. Human Press, Totowa, New Jersey, 16 pages.
Cooper, A. et al. (1994). "Isothermal Titration Microcalorimetry," located at <http://www.chem.gla.ac.uk/staff/alanc/MMB-ITC-1994.pdf> retrieved on Jan. 15, 2010. (14 pages).
Extended European Search Report dated Sep. 22, 2015, directed to EP Application No. 09830940.4; 5 pages.
Doyle, M. L. (1999). "Titration Microcalorimetry in Current Protocols in Protein Science, Supplement 18," located at <http://www.nshtvn.org/ebook/molbio/Current%20Protocols/CPPS/ps2004.pdf> retrieved on Jan. 15, 2010.
International Search Report and Written Opinion dated Feb. 9, 2009, directed to International Application No. PCT/US2008/081961; 6 pages.
MicroCal, LLC, "Autosampler for AutoITC User's Manual," *Ultrasensitive Calorimetry for the Life Science*, MAU190040; 44 pages.
Broga et al., Office Action dated Nov. 15, 2010, directed to U.S. Appl. No. 12/326,300; 18 pages.
Broga et al., Office Action dated Jun. 21, 2011, directed to U.S. Appl. No. 12/326,300; 20 pages.
Broga et al., Office Action dated Jul. 15, 2013, directed to U.S. Appl. No. 12/326,300; 19 pages.
Broga et al., Office Action dated Dec. 16, 2013, directed to U.S. Appl. No. 12/326,300; 22 pages.
Broga et al., Office Action dated Nov. 10, 2014, directed to U.S. Appl. No. 12/326,300; 22 pages.
Broga et al., Office Action dated Sep. 22, 2015, directed to U.S. Appl. No. 14/736,905; 9 pages.

\* cited by examiner

AUTOMATIC ISOTHERMAL TITRATION MICROCALORIMETER APPARATUS AND METHOD OF USE

CROSS REFERENCE TO RELATED APPLICATIONS

This application is a continuation of U.S. application Ser. No. 14/736,905, filed on Jun. 11, 2015, now U.S. Pat. No. 9,404,876, issued on Jul. 13, 2016, which is a continuation of U.S. patent application Ser. No. 12/326,300, filed on Dec. 2, 2008, now U.S. Pat. No. 9,103,782, issued on Aug. 11, 2015, the entire contents of which are hereby incorporated by reference.

BACKGROUND OF THE INVENTION

The present invention relates generally to microcalorimeters and more specifically to features that improve the performance of microcalorimeters, especially an automated isothermal titration micro calorimetry system (ITC system).

Microcalorimeters are broadly utilized in fields of biochemistry, pharmacology, cell biology, and others. Calorimetry provides a direct method for measuring changes in thermodynamic properties of biological macromolecules. Microcalorimeters are typically two cell instruments in which properties of a dilute solution of test substance in an aqueous buffer in a sample cell are continuously compared to an equal quantity of aqueous buffer in a reference cell. Measured differences between the properties of the two cells, such as temperature or heat flow, are attributed to the presence of the test substance in the sample cell.

One type of microcalorimeter is an isothermal titration calorimeter. The isothermal titration calorimeter (ITC) is a differential device, but operates at a fixed temperature and pressure while the liquid in the sample cell is continuously stirred. The most popular application for titration calorimetry is in the characterization of the thermodynamics of molecular interactions. In this application, a dilute solution of a test substance (e.g., a protein) is placed in the sample cell and, at various times, small volumes of a second dilute solution containing a ligand, which binds to the test substance, are injected into the sample cell. The instrument measures the heat, which is evolved or absorbed as a result of the binding of the newly introduced ligand to the test substance. From results of multiple-injection experiments, properties, such as, the Gibbs energy, the association constant, the enthalpy and entropy changes, and the stoichiometry of binding, may be determined for a particular pairing between the test substance and the ligand.

While currently utilized ITCs provide reliable binding data results, their widespread utilization in the early stages of drug development have been limited by several factors: the relatively high amounts of protein required to perform a binding determination (e.g., about 0.1 milligram (mg) to about 1.0 mg of a protein), the limited throughput due to the time required to perform the measurement and the complexity of using conventional ITCs.

Today, gathering binding data utilizing prior art ITCs require extensive preparation and skill by the practitioner. For example, using prior art ITCs, the reference and sample cells are first filled respectively with the reference substance and sample substance via a corresponding cell stem. Next, a titration pipette of the ITC is filled with a titrant, which is a delicate operation as it is very important that the syringe in the pipette is accurately filled and that there is no air trapped therein. Then a needle of the titration pipette is manually placed in the sample cell via the cell stem, and the ITC experiments can be initiated. The ITC measurement procedure is controlled by a control unit in the form of a computer or the like running a program for performing the experiments. Consistent with the program used for the experiment, a stirring motor rotates the syringe, needle, and paddle at an assigned speed enabling proper mixing of the reagents. Consistent with the program used for the experiment (e.g., when a certain temperature and/or equilibrium are reached), a plunger in the syringe is activated to inject the titrant into the sample solution. The injection can be done discretely (step-by-step) or continuously, depending on the program settings. The calorimeter continuously measures and records the heat release/absorption versus time associated with the interaction of reagents. The analysis of the results is done according to the established algorithm.

As would be appreciated by a reading of the above-described prior art procedure, utilizing prior art ITCs, the quality of binding measurements performed with these prior art ITCs depends heavily of the operator's skills and experience, and involves a considerable amount of preparation time.

For some time there has been at least one automated ITC system on the market, MicroCal AutoITC, which is based on a commercially available micro calorimeter and a linear robot system and a fluidics system arranged to perform automatic sample handling.

SUMMARY OF THE INVENTION

The object of the invention is to provide a new automatic isothermal titration micro calorimetry system (ITC system), which ITC system overcomes one or more drawbacks of the prior art. This is achieved by the ITC system as defined in the independent claims.

One advantage with the present ITC system is that each titration experiment requires less time compared to the prior art. This is e.g. due to the reduced cell volume and that washing and refilling of the pipette assembly and the sample cell is performed essentially in parallel. Hence the system throughput is considerably higher compared to the prior art systems, making it possible to evaluate large number of samples to make screening type experiments.

Another advantage is that the ITC system may be arranged to perform a large number of unattended titration experiments.

Embodiments of the invention are defined in the dependent claims.

DETAILED DESCRIPTION OF THE INVENTION

Figure 1:
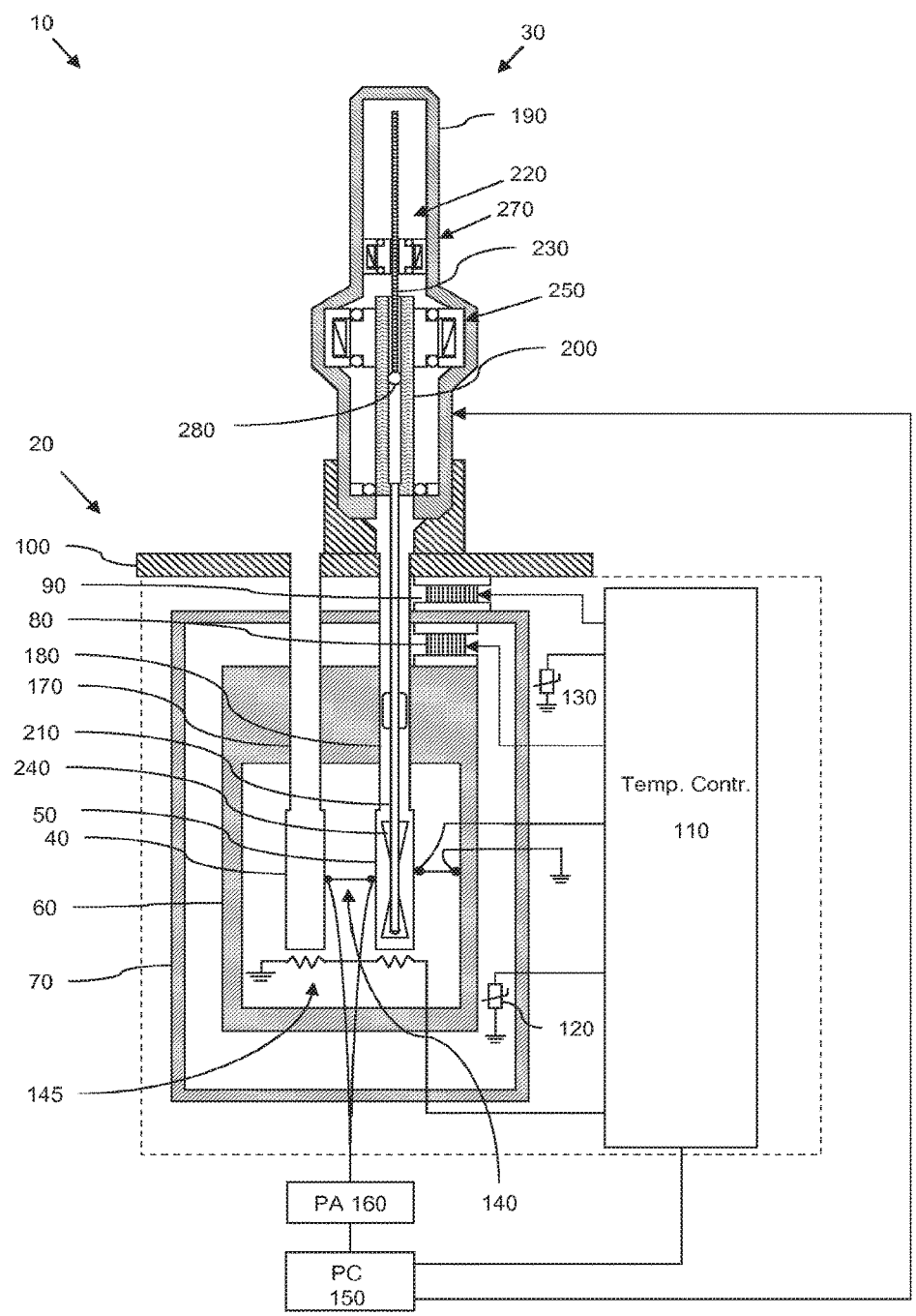
FIG. 1 shows a schematic example of a prior art manual ITC system in cross-section, the ITC system comprising an automatic pipette assembly.

In the PCT application PCT/US2008/081961, which is incorporated by reference, a manual ITC system 10 of the type disclosed in FIG. 1 is presented. According to one embodiment, the manual ITC system 10 is utilized as micro-calorimeter in the present automatic ITC system, but in other embodiments, the micro-calorimeter is of other types, as will be discussed in greater detail below. In the disclosed manual ITC system 10, the cell compartment volume is reduced by about a factor of seven as compared to prior art ITCs, without a reduction in sensitivity, and with a significantly faster response time. Such an ITC system permits the performance of experiments with about 10 times less protein sample, and with only a total of about 2 to about 4 titrations per hour. In addition to reducing the costs associated with running the ITC experiment, a smaller cell volume also extends the number of ITC applications. For example, the range of binding affinities that can be measured by ITC is dictated by a parameter called "c value," which is equal to the product of the binding affinity ($K_a$) and the total concentration ($M_{total}$) of macromolecule (c=[$M_{total}$]$K_a$). For accurate affinity determination, the c value must be between 1 and 1,000. A decrease in the cell volume by a factor of ten results in a similar increase in c value if the same amount of protein is used, and, consequently, the ability to measure weak binders. This ability is especially important in the early stages of drug discovery, in which binding affinities are weak, especially in conjunction with a fully automated instrument.

FIG. 1 schematically shows one embodiment of the manual ITC system 10 that may be automated in accordance with the present invention. The ITC system 10 comprises a micro calorimeter 20 and an automatic pipette assembly 30. The micro calorimeter 20 comprises a reference cell 40 and a sample cell 50 which are designed to be essentially identical in heat capacity and volume. The cells 40 and 50 are comprised of a suitable chemically inert and heat conductive material, such as gold, Platinum, tantalum, hastelloy or the like. The cells 40 and 50 may be of essentially any suitable shape, but it is desirable that they are of the same shape, that they are possible to arrange in a fully symmetric arrangement, and that efficient mixing of the titrant with the sample may be achieved. In the disclosed embodiment, the cross-section of the cells 40 and 50 is rectangular, and the cross-section in the transverse horizontal direction may be circular, resulting in coin shaped cells with circular facing surfaces.

In order to reduce any external thermal influences to a minimum, the, reference cell 40 and the sample cell 50 are both enclosed by a first thermal shield 60 which in turn is enclosed by a second thermal shield 70. The thermal shields 60, 70 may be comprised of any suitable thermally conductive material such as silver, aluminum, cupper or the like. The shields 60, 70 may further be comprised of one or more thermally interconnected sub shields (not shown, to provide even further stable temperature conditions for the calorimetric cells 40, 50.

In order to control the temperature of the shields 60, 70, thermal control means may be arranged to control the temperature thereof. In an ITC system said thermal control means are mainly used to set the "isothermal" temperature of the calorimeter, ie of the thermal shields 60, 70, before the titration experiments are initiated. But as will be disclosed in greater detail below, said thermal control means may also be used to improve the adiabatic behavior of the calorimeter. According to one embodiment, the thermal control means are comprised of one or more heat pump units, such as a thermoelectric heat pump device based on the peltier effect or the like. Other types of thermal control means include thermostatically controlled liquid baths, mechanical heat pumps, chemical heating or cooling systems or the like.

In the disclosed embodiment a first heat pump unit 80 is arranged to transfer heat energy between the first 60 and second thermal shields 70, a second heat pump unit 90 is arranged to transfer heat energy between the second thermal shield 70 and a heat sink 100 in thermal contact with the ambient temperature. A temperature controller 110 is arranged to control the first and second heat pump units 80, 90 so that the desired temperature conditions are achieved. The temperature controller 110 monitors the temperatures of the first 60 and second thermal shield by associated temperature sensors 120 and 130 respectively. Furthermore, the thermal controller 110 is arranged to control the cell temperature by a cell heating arrangement 145. The thermal controller 110 is controlled via a calorimeter user interface run on a computer 150 or the like. Calorimetric sensors 140 for sensing the temperature difference between the sample cell 50 and reference cell 40 during the ITC experiments may be connected to the computer 150, e.g. via a preamplifier 160.

A reference cell stem 170 and a sample cell stem 180 provides access to the reference cell 40 and sample cell 50, respectively, for supplying reference and sample fluids, titration fluid, washing of the cells etc. In the disclosed embodiment, the cell stems 170 and 180 both extends essentially vertically through both thermal shields and the heat sink to provide direct communication with cells 40 and 50 and the cell stems 170 and 180 each support their respective cell 40 and 50 in the cavity of the first thermal shield 60.

The automatic pipette assembly 30 comprises a pipette housing 190, a syringe 200 with a titration needle 210 arranged to be inserted into the sample cell 50 for supplying titrant, and a linear activator 220 for driving a plunger 230 in the syringe 200. The titration needle 210 is rotatable with respect to the housing 190 and is provided with a stirring paddle 240 arranged, to stir sample fluid in the sample cell 50 in order to achieve efficient mixing of titrant and sample fluid. The automatic pipette assembly 30 further comprises a stirring motor 250 for driving the rotation of the titration needle 210.

In the embodiment disclosed in FIG. 1 the stirring motor 250 is a direct drive motor with a hollow rotor arranged concentric with the syringe 200 and the titration needle 210. The syringe 200 is at its upper end supported for rotation by the stirring motor 400 and at the lower end by a bearing 260.

In an alternative embodiment, not shown in the figures, the stirring motor 250 drives the titration needle for rotation by a rotation transmission arrangement, such as a drive belt arrangement, a drive wheel arrangement or the like. Moreover, the stirring motor may be arranged separated from the pipette assembly 30 and be arranged to drive the titration needle for rotation by a suitable transmission arrangement such as a magnetic coupling or the like.

The automatic pipette assembly 30 is controlled by a controller of the ITC system, e.g. stirring of the sample and the titration.

In the disclosed embodiment, the linear activator 220 comprises a stepper motor 270 arranged to drive the threaded plunger 230 that extends coaxially through the hole of a hollow rotor and into the syringe 200 wherein it is rotatably attached to a pipette tip 280 that seals against the inner wall of the syringe 200 to allow displacing a precise volume of titration liquid from syringe 200. The linear activator 220 may be of any other type capable of perform controlled linear motion with sufficient precision. This design allows syringe to be rotated independently of the main body 190 of the pipette assembly 30; at the same time, the linear activator 220 can drive the threaded plunger 230.

In accordance with one embodiment, schematically disclosed in FIGS. 2 to 8*d*, there is provided an automated isothermal titration micro calorimetry (ITC) system 300 comprising:
- a micro calorimeter 20 with a sample cell 50 and a reference cell 40, the sample cell 50 is accessible via a sample cell stem 180 and the reference cell 40 is accessible via a reference cell stem 170,
- an automatic pipette assembly 30 comprising a syringe 200 with a titration needle 210 arranged to be inserted into the sample cell 50 for supplying titrant, the pipette assembly 30 comprises a linear activator 220 for driving a plunger 230 in the syringe 200,
- a pipette translation unit 310 supporting the pipette assembly 30 and being arranged to place pipette in position for titration, washing and filling operations,
- a wash station 320 for the titrant needle 210, and
- a cell preparation unit 330 arranged to perform operations for replacing the sample liquid in the sample cell 50 when the pipette 30 is placed in another position than the position for titration.

The micro calorimeter 20 may be of any type capable of performing ITC calorimetric measurements using sufficiently small volumes of sample such as the micro calorimeter 20 schematically shown in FIG. 1. As disclosed above (FIG. 1), but not specifically shown in FIGS. 2 to 8*d*, a micro calorimeter generally comprises a sample cell 50 and a reference cell 40, wherein the sample cell 50 is accessible via a sample cell stem 180 and the reference cell 40 is accessible via a reference cell stem 170 (shown as circular openings in FIG. 2). The automatic pipette assembly 30 may be of the type disclosed above, but it may be of any suitable design comprising a syringe 200 with a titration needle 210 arranged to be inserted into the sample cell 50 for supplying titrant. Like above, the pipette assembly 30 may further comprise a linear activator 220 for driving a plunger 230 in the syringe 200. However, the syringe 200 may be of essentially any type, capable of providing well-defined volumes of titrant. The titration needle 210 may be rotatable and may be provided with a paddle 240 for stirring of the liquid in the sample cell 50 during the titration. The stirring may be accomplished as is discussed above or in any other suitable way.

Figure 2:
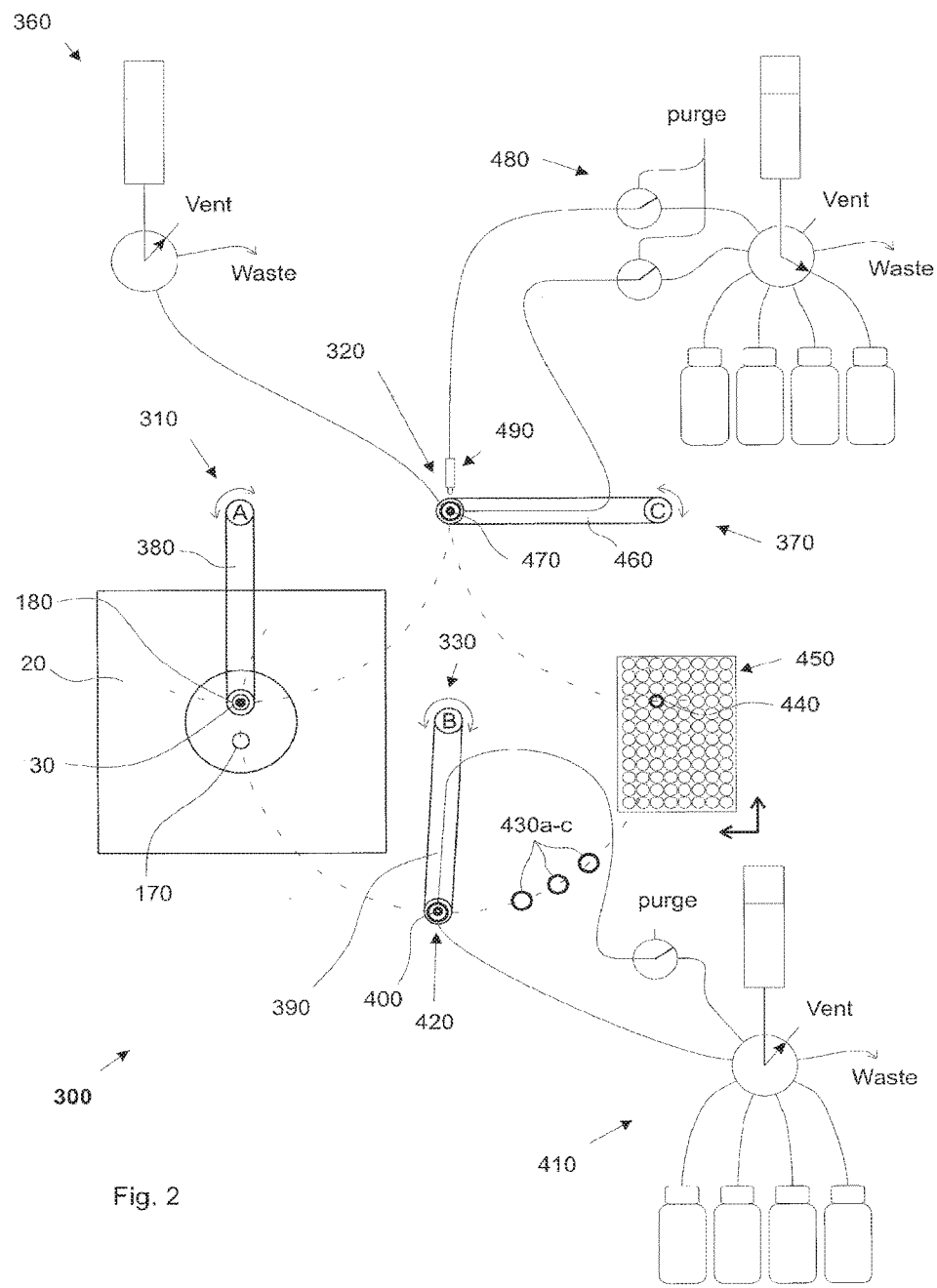
FIG. 2 shows a schematic view of one embodiment of an automated ITC system.

The pipette translation unit 310 may be of any type capable of placing the pipette in the appropriate positions for titration, washing and filling. FIGS. 2 and 3 schematically show two different types of translation units, wherein FIG. 2 shows a rotation translation unit 310 and FIG. 3 shows a linear translation unit 310*b*. In order to place (insert) the titration needle 210 in position in the sample cell 50, and/or in other positions, the pipette translation unit 310 is capable of moving the pipette 30 in the vertical direction with respect to the micro calorimeter 20. The pipette translation unit 310 may be mechanically restricted with respect to its freedom of movement so that it only may move between mechanically predetermined positions, or it may be a general translation unit of robot type that is restricted to movement between said predetermined positions by means of software parameters, or a combination thereof. For clarity reasons no such means for vertical movements have been included in the FIGS. 2 to 8*d*.

The wash station 320 is arranged at a suitable position wherein the titration needle 210 of the pipette assembly 30 can be placed in position for washing. The wash station 320 may be of any suitable type capable of washing at least the section of the titration needle 210 that is immersed in the sample during titration when the pipette assembly 30 is placed in position for washing. According to one embodiment, the wash station 320 comprises a wash cavity 340 arranged to receive the titration needle. The wash station 320 is made of any suitable material that is inert with respect to the reagents used in the ITC experiments and the wash cycles. According to one embodiment, the wash station 320 comprises a waste outlet port 350 at the bottom end of the wash cavity connected to a waste removal unit 360. The waste outlet port 350 is used to remove waste liquids as well as wash liquids during the pipette washing cycle, as will be disclosed more in detail below, and it is preferably arranged at the bottom end of the wash cavity 340 in order to enable complete drainage of the wash cavity. In one embodiment not disclosed in the figures, the pipette translation unit 310 is limited to movement in the vertical direction, and the wash station 320 instead is arranged to be moved to a position in alignment with the needle 240 for cleaning of the same.

In FIGS. 2 to 8*d* the cell preparation unit 330 is shown as a translation unit of the same type as the pipette translation unit 310, but arranged to be positioned in at least two positions related to washing and replacing sample liquid in the sample cell. By the provision of a cell preparation unit 330 for replacing the sample liquid in the sample cell 50 the total cycle time is reduced and thus the throughput of the ITC system 300 is increased, as the sample cell 50 may be washed and filled with new sample liquid at the same time as the pipette 30 is washed and filled with new titrant.

FIG. 2 schematically discloses an automated isothermal titration micro calorimetry (ITC) system 300 according to one embodiment of the present invention. As mentioned above, the translation units 310, 330, 370 in this embodiment are all of rotary type, and all positions of operation are arranged along circular paths of the rotary translation units. In another embodiment, not shown, one or more of the rotary translation units are provided with additional linear translation means to extend work area and to increase the flexibility.

In FIG. 2 the pipette translation unit 310 comprises a pipette arm 380 that is rotatably supported for rotation about an axis A, and supporting the pipette assembly 30 at the other end thereof. The pipette arm 380 is further arranged to move the pipette vertically, either in that the arm 380 can be moved vertically along the axis A, or in that the arm 380 is limited for rotation in one plane and the pipette 30 is vertically moveable with respect to the arm 380. The pipette arm 380 is arranged to place pipette 30 in position for:
- titration with the titration needle inserted into the sample cell 50,
- washing and filling with the titration needle inserted in a combined wash/fill station 320.

The combined wash/fill station 320 may be a wash station of the type discussed above with an outlet port 350 at the bottom end of the wash cavity 340. The outlet port 350 is connected to a waste fluidics system 360 that will be discussed in more detail below.

The cell preparation unit 330 is in turn comprised of a corresponding cell arm 390 that is rotatably supported for rotation about an axis B, supporting a cell cannula 400 connected to a cell fluidics system 410 for dispensing and withdrawing liquid in the sample cell 50 and potentially also in the reference cell 40. The cell fluidics system 410 will be disclosed in more detail below. The cell arm 390 is arranged to move the cell cannula 400 to a plurality of positions such as the cells, 40, 50 of the micro calorimeter, one or more sample sources, and a sample preparation station 420, or the like. In the disclosed embodiment, four different sample source positions are included of which three positions represent large volume sample reservoirs of vial type 430a-430c, e.g. for standard sample liquids, and the fourth position an autosampler position 440, e.g. for specific or sensitive sample liquids, wherein the cell cannula 400 is arranged to draw the sample liquid from a specific well in a sample tray 450 (e.g. micro plate or the like). In the disclosed embodiment, the autosampler position 440 is a static position to which the cell cannula 400 can be moved by the cell arm 390 and be lowered into a specific well of a sample tray 450 that can be moved to position a selected well at the autosampler position 440 by a tray actuator (not shown). The tray actuator may be of any suitable type capable of selectively position a specific sample well of a sample tray 450 at a desired position, such as a linear X-Y actuator or a rotary actuator with a carousel tray. The sample preparation station 430 may be used to prepare the sample before it is transferred into the cell 50 or 40, e.g. by bringing the sample to a temperature close to the experimental temperature, or by degassing through mixing.

The ITC system 300 disclosed in FIG. 2 further comprises a titrant transfer unit 370 arranged to transfer titrant from a primary titrant source, e.g. a sample tray 450, to the wash/fill station 320. In the disclosed embodiment, the transfer unit 370 comprises a titrant transfer arm 460, e.g. corresponding to the cell transfer arm 380, that is rotatably supported for rotation about an axis C, supporting a transfer cannula 470 connected to a syringe fluidics system 480. The titrant transfer arm 460 is arranged to position the titrant cannula 470 in an autosampler position 440 for drawing a titrant sample from a titrant well in a sample tray 450, and in position to dispense said titrant sample in the wash/fill station 320. The autosampler position 440 and the sample tray 450 may be a separate position and tray with respect to the cell cannula autosampler position 440 discussed above, but as is disclosed in FIG. 2, the cell cannula 470 and the titrant cannula 400 may be positioned at the same autosampler position 440 (not at the same time) and the tray actuator may be controlled to position appropriate wells for the respective cannula at the autosampler position 440. The syringe fluidics system 480 is further connected to a fill port connection unit 490 being arranged to selectively connect to a fill port 500 at an upper section of the syringe 200 in the pipette assembly. When connected to the fill port 500, the fill port connection unit 490 provides fluidic contact between the syringe cavity and the syringe fluidics system 480 to selectively pull or push liquid or gas through the syringe 200.

Figure 3A:
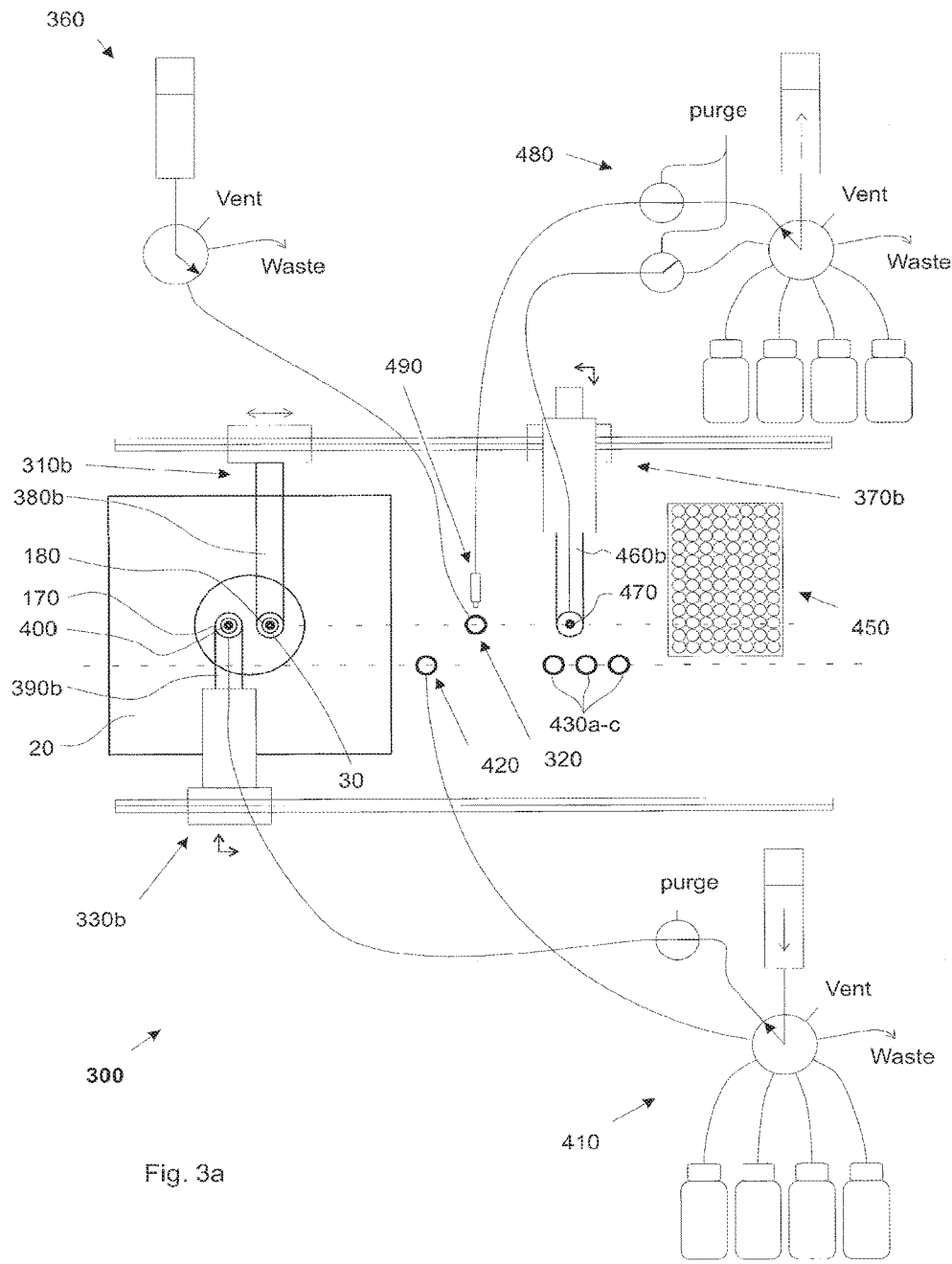
FIGS. 3a and 3b show schematic views of other embodiments of the automated ITC system.
Figure 3B:
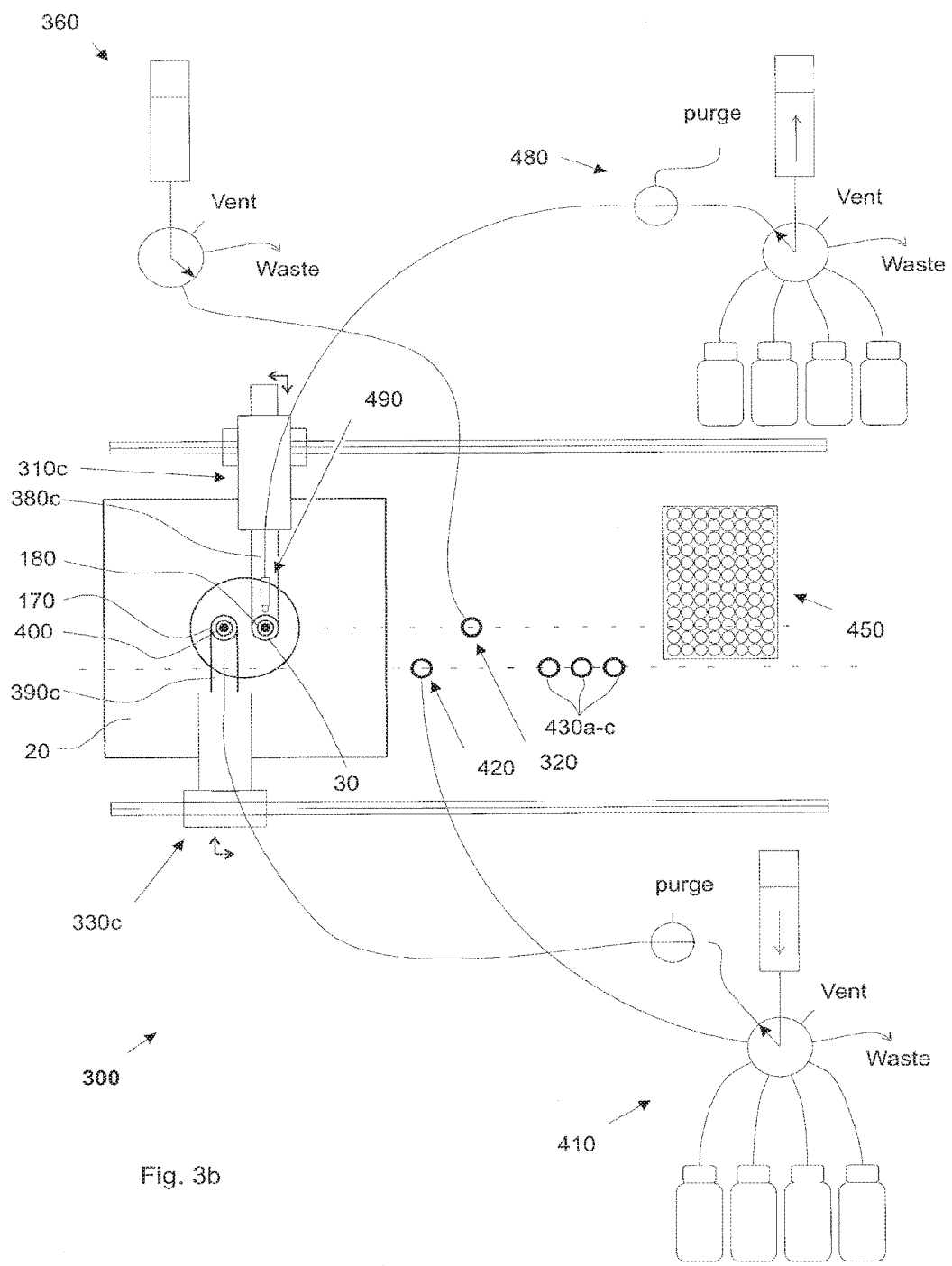

As previously mentioned, FIG. 3a shows an ITC system corresponding to the system of FIG. 2, but wherein the translation units 310b, 330b, 370b for the pipette 30, cell cannula 400 and transfer cannula 470 are of linear type, and the associated positions of operations are arranged accordingly. Moreover, the cell arm 390b and the transfer arm 460b are moveable in two dimensions (disregarding the vertical direction as mentioned above) whereby one or both may be controlled to position the associated cannula in a selected well in a static sample tray 450. FIG. 3b shows an embodiment of a linear ITC-system similar to FIG. 3a, wherein the titrant transfer unit is omitted and the pipette translation unit 310c is arranged to place the pipette 30 in position for filling directly from a selected well in the sample tray 450. Moreover, the fill port connection unit 490 is arranged by the pipette 30 on the pipette arm 380c in order to connect to the fill port 500 both when the pipette 30 is placed in the wash station 320 and in a fill position in a well of the sample tray 450.

Figure 4A:
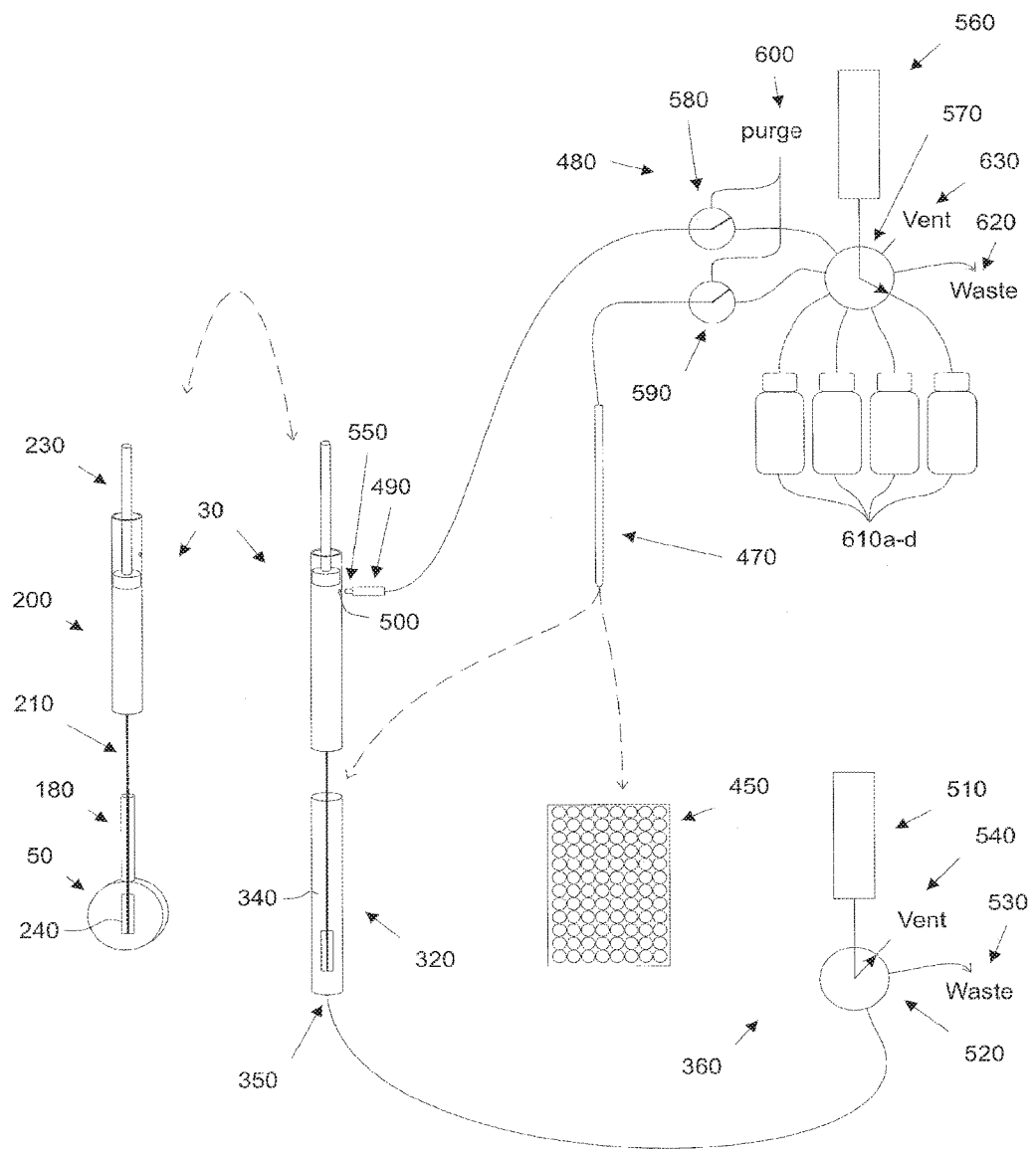
FIGS. 4a and 4b show schematic views of two embodiments of a syringe fluidics system for an automated ITC system.

As mentioned above, the waste fluidics system 360 is connected to the outlet port 350 of the wash station 320 for withdrawing fluid from the wash station. According to one embodiment, the waste fluidics system 360 comprises a waste pump 510 for selective withdrawal of fluid from the wash station 320, optionally in combination with one or more controllable valves 520 to direct the flow of waste fluids. In other embodiments, the waste pump may be a common pump for one or more fluidics systems in the ITC system 300, and one or more valves may control the flow in the systems, respectively. The waste pump 510 may be any suitable pump capable of removing the fluids in the wash station, such as a peristaltic pump, a syringe pump or the like. FIG. 4a shows a schematic view of an embodiment of a waste fluidics system 360 comprising a waste pump 510 of reservoir type, such as a syringe pump, and a waste control valve 520 for selective connection disconnection of the waste pump to the outlet port 350, a waste outlet 530 and a vent port 540.

As mentioned above, and shown more in detail in FIGS. 4a to 5c, the syringe 200 of the pipette may comprise a fill port 500 at an upper section thereof, providing fluidic contact with the syringe cavity when the plunger 230 is positioned above said fill port 500. Further the ITC system 300 may comprise a mating fill port connection unit 490 being arranged to selectively connect to the fill port 500, thereby providing fluidic contact between the syringe cavity and a syringe fluidics system 480 arranged to selectively pull or push liquid or gas through the syringe as part washing and filling operations, which will be disclosed more in detail below. As is schematically disclosed, the fill port 500 may be a bore through a wall of the syringe 200, and the bore may be of any suitable shape such as straight or conical. The connection unit 490 comprises a connection member 550 mating shape and/or of resilient material to achieve a reliable and fluid tight connection. The syringe fluidics system 480 may further be connected to the transfer cannula 470, and arranged to control aspiration and dispensing of fluids during titrant transfer operations, as well as washing operations of the transfer cannula 470.

Figure 4B:
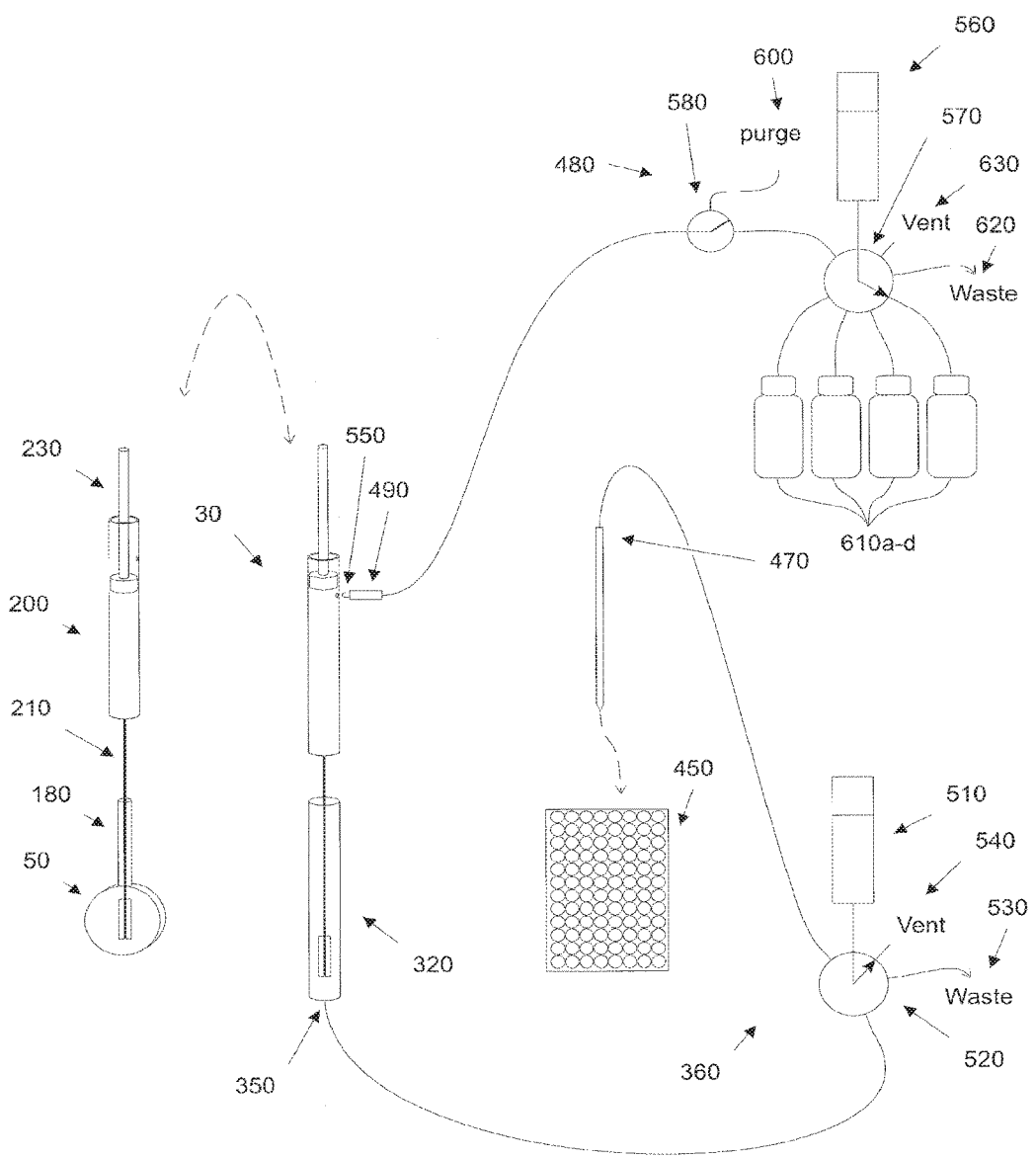

According to one embodiment, the syringe fluidics system 480 comprises a fill pump 560 to selectively pull or push liquid in the fluidics system, optionally in combination with one or more controllable valves 570, 580, 590 to direct the flow of fluids and a purge gas source 600. In other embodiments, the fill pump may be a common pump for one or more fluidics systems in the ITC system 300, and one or more valves may control the flow in the systems, respectively. The waste pump 560 may be any suitable pump capable of push or pull the liquids in the syringe fluidic system with relatively high accuracy, such as a peristaltic pump, a syringe pump or the like. FIG. 4a shows a schematic view of an embodiment of a syringe fluidics system comprising a fill pump 560 of reservoir type, such as a syringe pump, a syringe control valve 570, syringe purge valve 580 and a transfer cannula purge valve 590. The syringe control valve 570 provides selective connection disconnection of the fill pump 560 to the fill port 500 of the syringe 200, to the transfer cannula 470, to a plurality of reagent reservoirs 610*a-d*, to a waste outlet 620 and to a vent port 630. The reagent reservoirs 610*a-d* may comprise wash liquids for washing the syringe 210 and/or the transfer cannula 470 or the like. FIG. 4*b* shows a schematic view of another embodiment of the syringe fluidics system 480 and the waste fluidics system 360, wherein the transfer cannula 470 is not connected to the syringe fluidics system 480, but instead connected to the waste fluidics system 360, whereby the titrant sample is transferred from the transfer cannula 470 to the wash station 320 via the waste fluidics system and the outlet port 350 of the wash station. Further, FIGS. 4*a* and 4*b* schematically show the pipette assembly 30 in position for titration, with the titration needle 210 inserted into the sample cell 50.

Figure 5A:
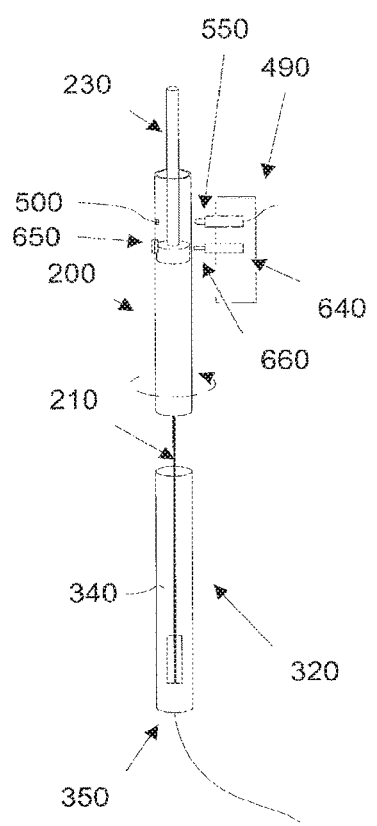
FIGS. 5a to 5c show schematic views of the function of a syringe fill port connector unit according to an embodiment.
Figure 5B:
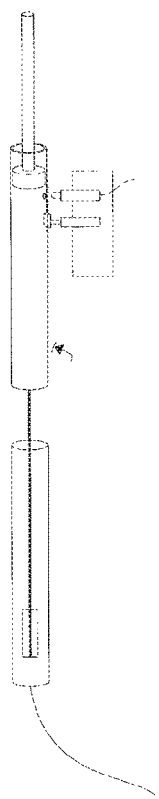
Figure 5C:
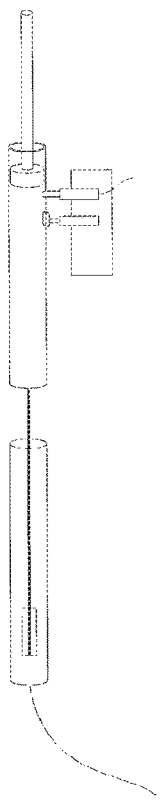

In some embodiments, as is previously discussed, the syringe 200 is rotatable with respect to the automatic pipette 30 and is driven for rotation by a stirring motor 250. Then, in order to locate the position of the fill port 500, the fill port connection unit 490 may comprise a port alignment mechanism 640 arranged to prevent rotation of the syringe at a predetermined angular position when a connection member 550 of the connection unit is aligned with the fill port 500. FIGS. 5*a* to 5*c* schematically shows an example of art alignment mechanism 640, wherein the syringe 200, or any other part that is arranged to rotate with the syringe 200, is provided with an alignment member 650, and the fill port connection unit 490 is provided with a rotation stop unit 660 that may be actuated to interfere with the rotation path of the alignment member 650, and when the alignment member 650 abuts the rotation stop unit 660, then the connection member 550 is aligned with the fill port 500. The alignment procedure comprises the steps of:

actuating the stop unit 660 (FIG. 5*a*), rotating the syringe slowly in a predetermined direction until further rotation is prevented by the stop unit 660 abutting the alignment member 650 (FIG. 5*b*), and actuating the connection member 550 to connect to the fill port 500 (FIG. 5*c*).

The stop unit 660 and the connection member 550 may be actuated by electromagnetic drive actuators in the form of an electric motor arrangement, a solenoid or the like, or they may be actuated by a hydraulic or pneumatic actuator or the like capable of moving the stop unit 660 and the connection member 550. In order to achieve a fluid tight connection between the syringe fill port 500 and the syringe fluidics system 480, the connection member 550 is pressed against the fill port 500 with a predetermined force. In one embodiment (not shown) the connection member 550 is actuated by an electromagnetic drive actuator, to move the connection member 550 into contact with the fill port and the connection member 550 is spring loaded with respect to the actuator, whereby the scaling force is determined by the spring constant and the compression of said spring.

As is e.g. disclosed in FIG. 2, the fill port connection unit 490 may be arranged at the wash station 320 to enable connection between the syringe cavity and the syringe fluidics system 480 when the pipette assembly 30 is arranged at the wash station 320. But, as is disclosed in FIG. 3*b*, the fill port connection unit 490, may be arranged together with the pipette assembly 30 supported by the pipette translation unit 310, whereby fluidic connection between the syringe fill port 500 and the syringe fluidics system 480 may be established in any position of operation.

According to one embodiment, the ITC system 300 is arranged to utilize the syringe fill port 500 to wash the syringe 200 and the titration needle 210 by pushing one or more wash liquids through the syringe 200 and the titration needle 210 via the syringe fill port 500 when the titration needle 210 of the pipette 30 is arranged in the wash cavity 340 of the wash station 320. Thereafter the system may dry the syringe 200, needle 210 and the wash station 320 by purging gas through the syringe 200 and the titration needle 210 via the syringe fill port 500 after washing the same.

In many situations it is important to fill the syringe 200 of the pipette assembly 30 with titrant without having any trapped air in the syringe 200. In one embodiment, this is achieved by pulling a predetermined volume of titrant into the syringe from a titrant source, e.g. the wash station 320, in which the titration needle 210 is inserted, wherein the predetermined volume is selected to be larger than the syringe volume, whereby the syringe is overfilled and the titrant start to exit the syringe through the fill port 500. Then the linear activator 220 is activated to close the fill port 500 by moving the plunger 230 below to the fill port 500.

Figure 6:
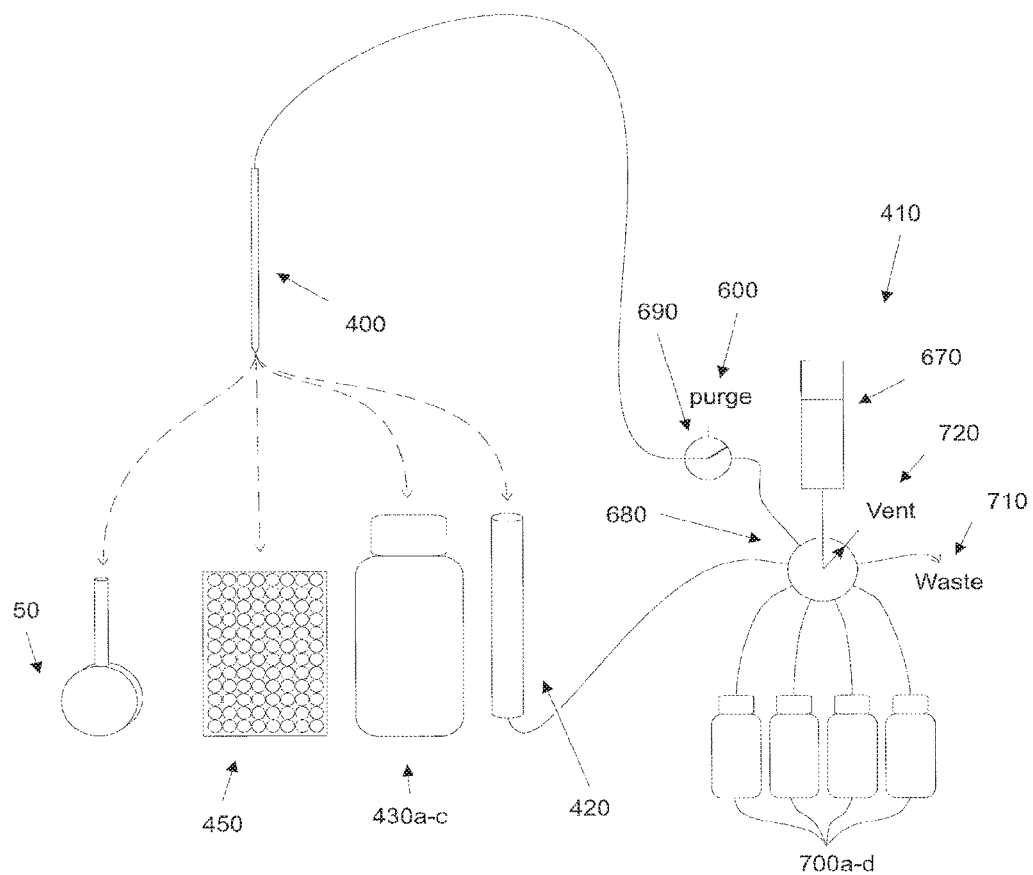
FIG. 6 shows a schematic view of a cell preparation fluidics system according to one embodiment.

FIG. 6 schematically shows an example of a cell fluidics system 410 connected to the cell cannula 400 for dispensing and withdrawing liquid in the sample cell 50 and potentially also in the reference cell 40. As is previously discussed, the cell cannula 400 may be arranged to be positioned in the sample cell 50, in a well of a sample tray 450, in one or more large volume sample reservoirs 430*a-c* and a sample preparation station 420. According to one embodiment, the cell fluidics system 410 comprises a cell pump 670 for selective dispensing and withdrawing of fluid through the cell cannula 400, optionally in combination with one or more controllable valves 680, 690 to direct the flow of cell wash fluids or the like. In other embodiments, the cell pump 670 may be a common pump for one or more fluidics systems 360, 380, 410 in the ITC system 300, and one or more valves may control the flow in the systems, respectively. The cell pump 670 may be any suitable pump capable of dispensing and withdrawing the fluids in e.g. the sample cell 50, such as a peristaltic pump, a syringe pump or the like. FIG. 6 shows a schematic view of an embodiment of a cell fluidics system 410 comprising a cell pump 670 of reservoir type, such as a syringe pump, a cell preparation control valve 680 for selective connection disconnection of the waste pump to the cannula 400, four cell wash liquid reservoirs 700*a-c*, a waste outlet 710 and a vent port 720, and a purge select valve 690 for connection of the cannula 400 to the cell preparation valve 680 or a source of purge gas 600 for drying the cannula 400.

Figure 7:
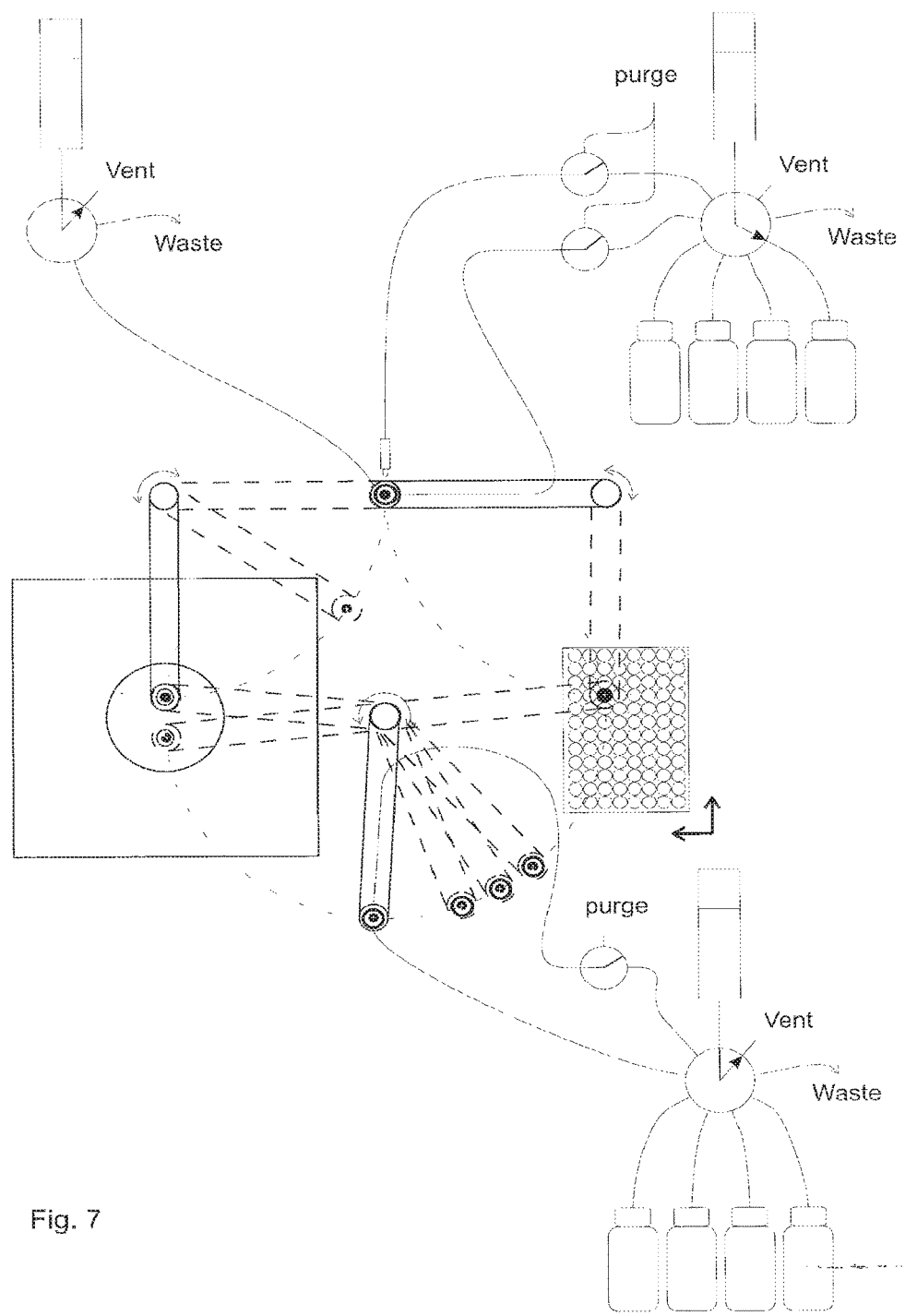
FIG. 7 schematically shows different states of operations for the ITC system of FIG. 2

FIG. 7 schematically shows the ITC system of FIG. 2 wherein positions of operation for each translation arm is shown by broken lines.

FIGS. 8*a* to 8D schematically show examples of states wherein operations for preparation of the pipette and the sample cell may be performed in parallel in the ITC system of FIG. 2.

Figure 8A:
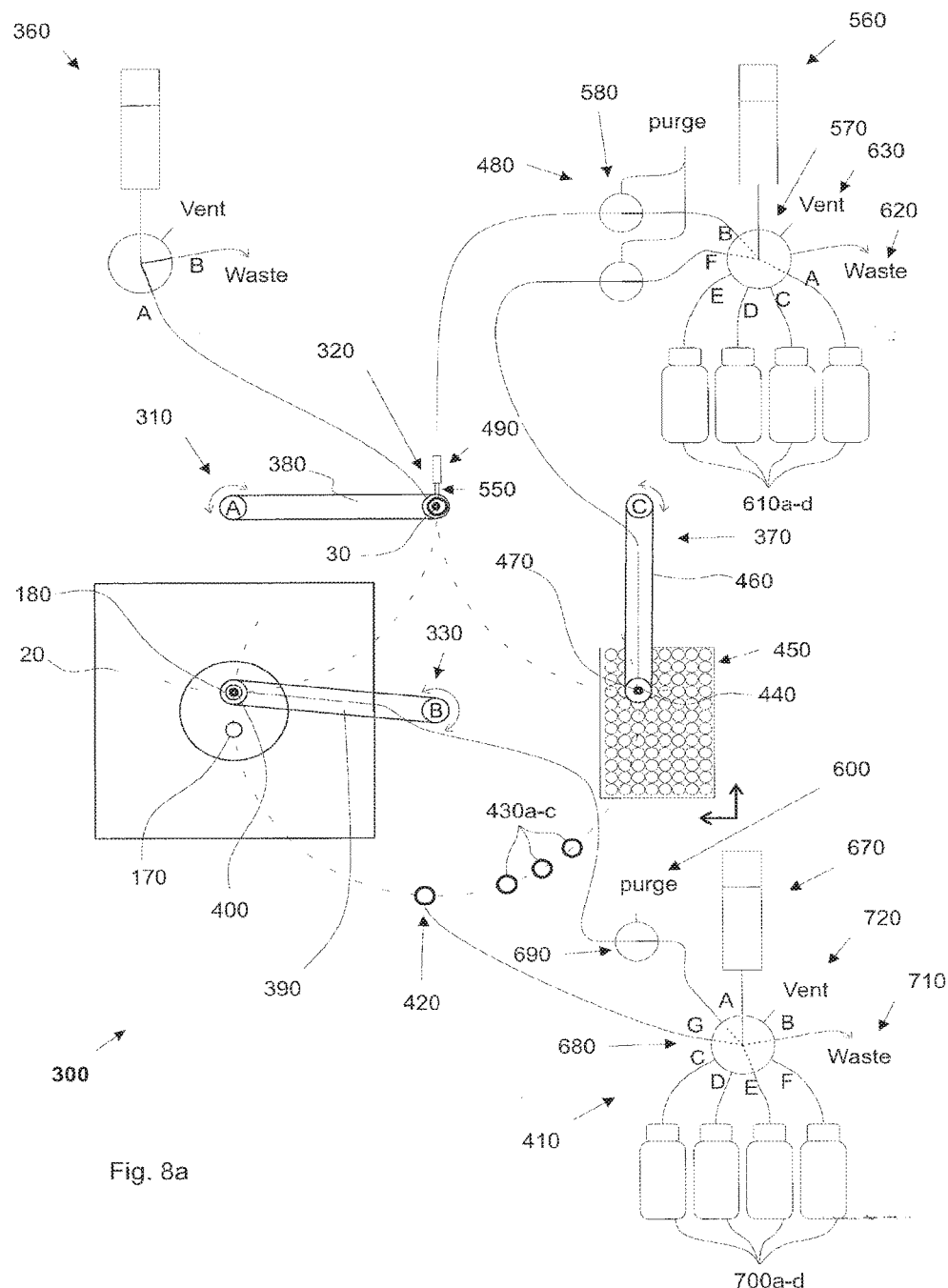
FIGS. 8a to 8d shows different states of operations for the ITC system of FIG. 2 more in detail.

In FIG. 8*a* the pipette assembly 30 is placed at the wash position with the titration needle 210 in the wash station 320 for a syringe wash cycle. During a wash cycle, the connection member 550 of the fill port connection unit 490 is connected to the fill port 500 of the syringe 200, and the syringe fluidics system 480 is arranged to push and pull one or more washing liquids through the syringe 200 optionally followed by purging a gas, e.g. nitrogen, through the syringe to dry the syringe 200. To push a wash liquid through the syringe, firstly the syringe control valve 570 is arranged in position A to connect the fill pump to the appropriate reagent reservoir 610a-d and the fill pump 560 is actuated to draw wash liquid into its pump reservoir, secondly the syringe control valve 570 is arranged in position B to connect the fill pump 560 to the fill port 500 of the syringe 200 and the fill pump 560 is actuated to push wash liquid through the syringe 200, whereby the wash liquid is dispensed from the titration needle 210 into the wash station 320. A full syringe cleaning cycle might comprise pushing the same or a different wash liquid (syringe valve positions C-E) two or more times through the syringe 200, and it may further involve pulling liquid from the wash station 320 through the syringe 200 and into the pump reservoir whereby it can be pushed through the syringe 200 one more time, or be discarded through the waste outlet 620 of the syringe fluidics system 480. When the fill pump 570 is arranged to consecutively push two or more different wash liquids through the syringe 200, the fill pump 570 may be rinsed to avoid contamination between washing liquids, by filling the pump reservoir with a rinse liquid, e.g. water. Liquid that is dispensed into the wash station 320 may be selectively withdrawn through the outlet port 350 by the waste pump 510 into the pump reservoir by setting the waste valve 520 in position A, and may thereafter be discarded through the waste outlet 530 by setting the waste valve 520 in position B.

In FIG. 8a, while the syringe wash cycle is performed at the wash station 320, the titrant transfer unit 370 is arranged to draw titrant sample from a well in the sample tray 450 by setting the syringe valve 570 in position F and pulling titrant from the well using the fill pump 560. The operation of drawing titrant from the well may e.g. be performed when the syringe 200 is purged with dry gas, whereby the fill pump 560 and the syringe valve 570 are not involved in the wash cycle, but after the fill pump 560 and the syringe valve 570 has been thoroughly rinsed and washed to avoid contamination.

In FIG. 8a, also while the syringe wash cycle is performed at the wash station 320, the cell preparation unit 330 is arranged to remove the previous sample from the sample cell 50 and to wash the sample cell 50. As the pipette assembly 30 is removed from the sample cell 50, the cell cannula 400 may be inserted into the sample cell 50, and by arranging the cell preparation control valve 680 in position A the cell pump 670 may be activated to withdraw the previous sample into the pump reservoir, and the previous sample may thereafter be discarded through the waste outlet 710 by setting the cell preparation control valve 680 valve in position B. Cleaning of the cell is thereafter performed by dispensing and withdrawing one or more cell wash liquids in the sample cell 50 optionally followed by purging a gas, e.g. nitrogen, through the cell cannula to dry the sample cell 50. To dispense a wash liquid in the sample cell, firstly the cell preparation control valve 680 is arranged in position C, D, E or F to connect the cell pump 670 to the appropriate wash liquid reservoir 700a-d and the cell pump 670 is actuated to draw wash liquid into its pump reservoir, secondly the cell preparation control valve 680 is arranged in position A to connect the cell pump 670 to the cannula 400 and the cell pump 670 is actuated to dispense wash liquid in the sample cell 50 through the cell cannula 200. The cleaning liquid(s) are thereafter withdrawn and discarded through the waste port 710 of the cell preparation control valve 680. According to the disclosed embodiment, the cell cannula 400 stays in the sample cell during the cell wash procedure, thereby the cell cannula 400 is washed at the same time as the cell 50 and is ready for transfer of fresh sample liquid to the sample cell 50.

Figure 8B:
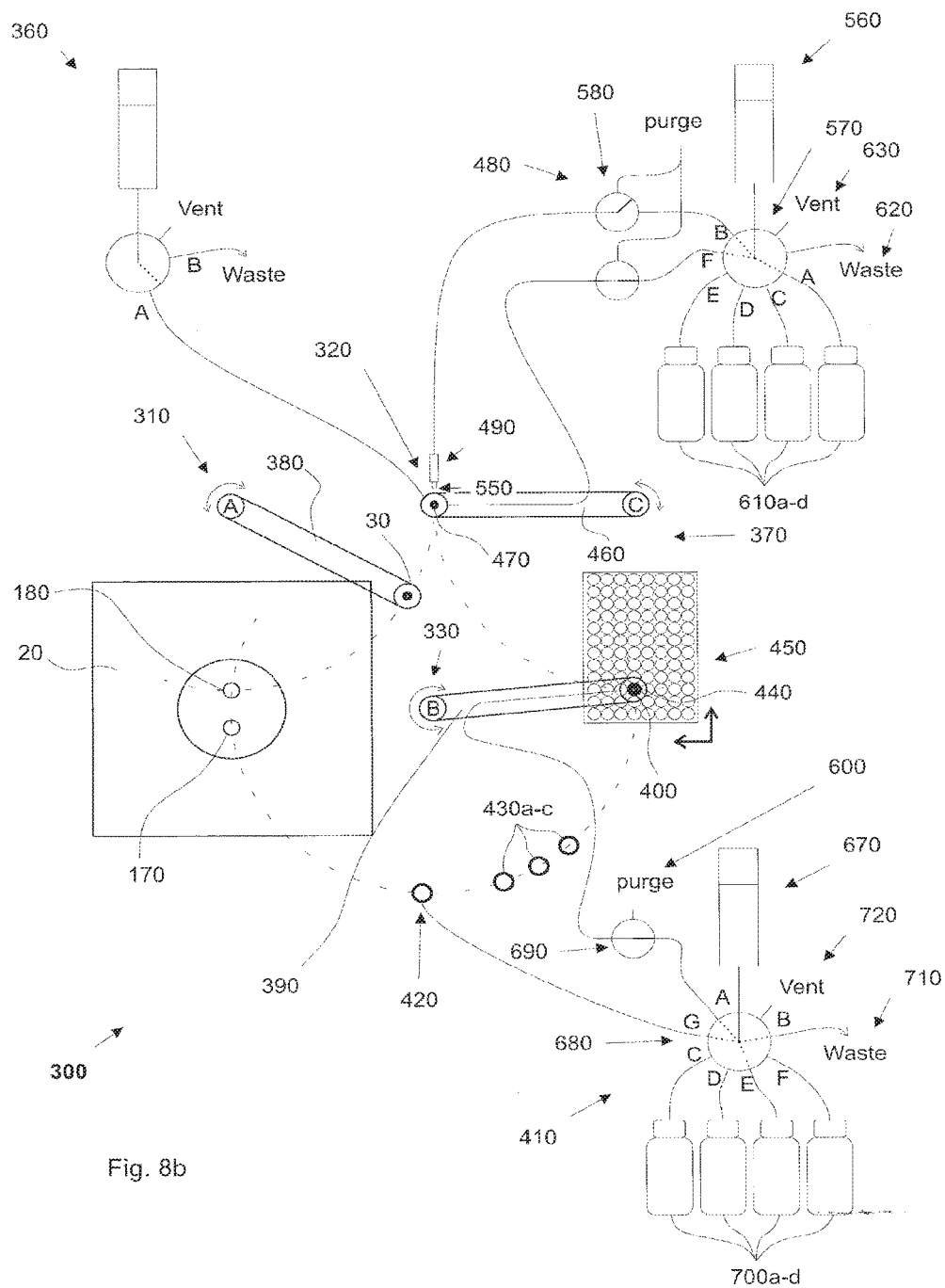

In FIG. 8b the pipette assembly 30 is placed at an intermediate position between the sample cell 50 and the wash station 320, in order to grant the titrant transfer cannula 470 of the titrant transfer unit 370 access to the wash station 320 to dispense a new titrant sample therein, and to grant the cell cannula 400 cell preparation unit 300 access to the sample cell 50 to fill the sample cell with fresh sample in the next step. The titrant transfer unit 370 is arranged to dispense the titrant sample from the cannula 470 into the wash station by setting the syringe valve 570 in position F and dispensing titrant using the fill pump 560.

In FIG. 8b the cell preparation unit is arranged to draw fresh sample from a well in the sample tray 450 by inserting the cell cannula 400 in a selected well containing the desired fresh sample, setting the cell preparation control valve 680 in position A and pulling fresh sample from the well into the pump reservoir of the cell pump 670. Alternatively, the cell cannula 400 may be inserted into one of the sample reservoirs 430a-c.

Figure 8C:
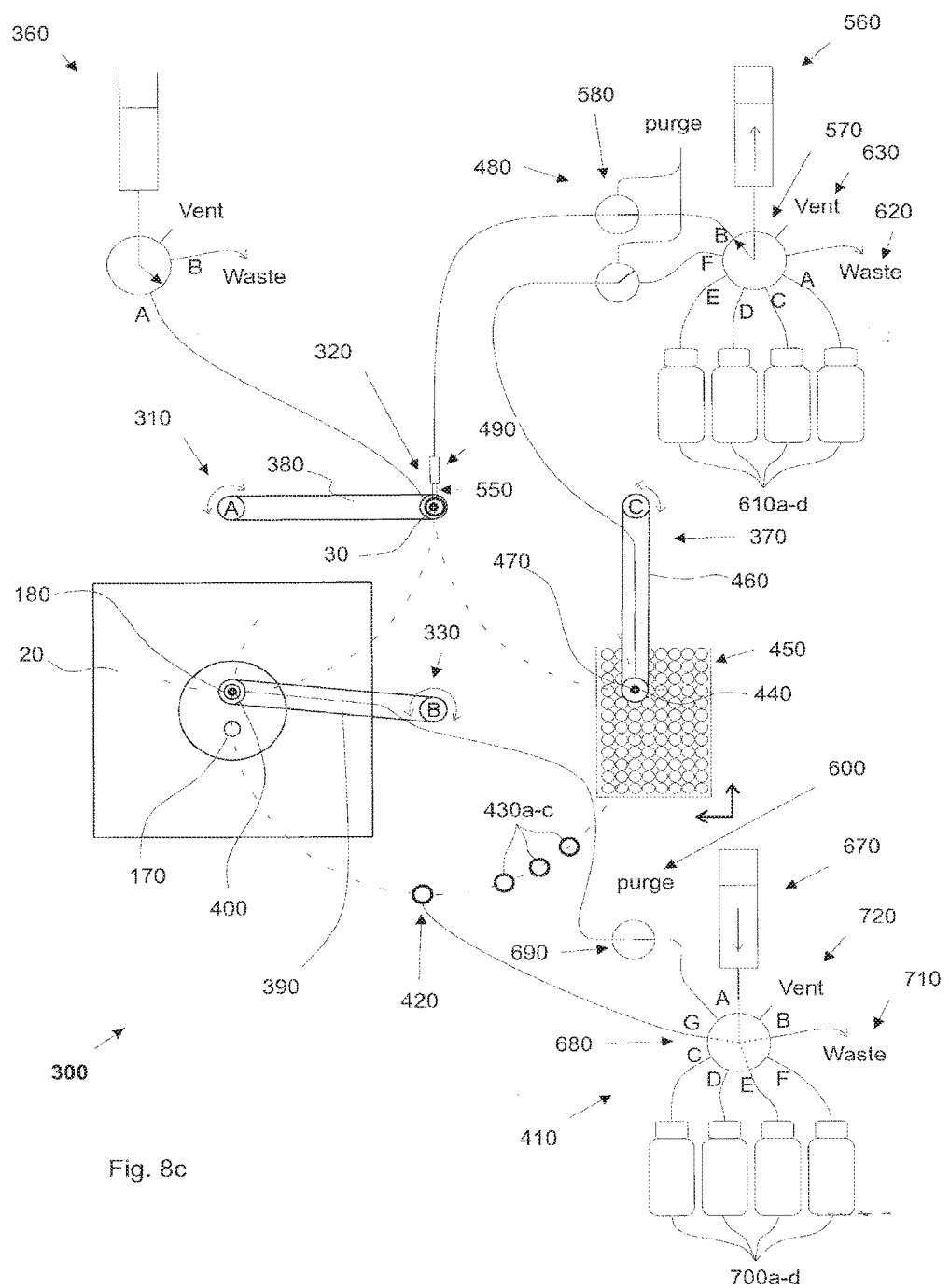
Figure 8D:
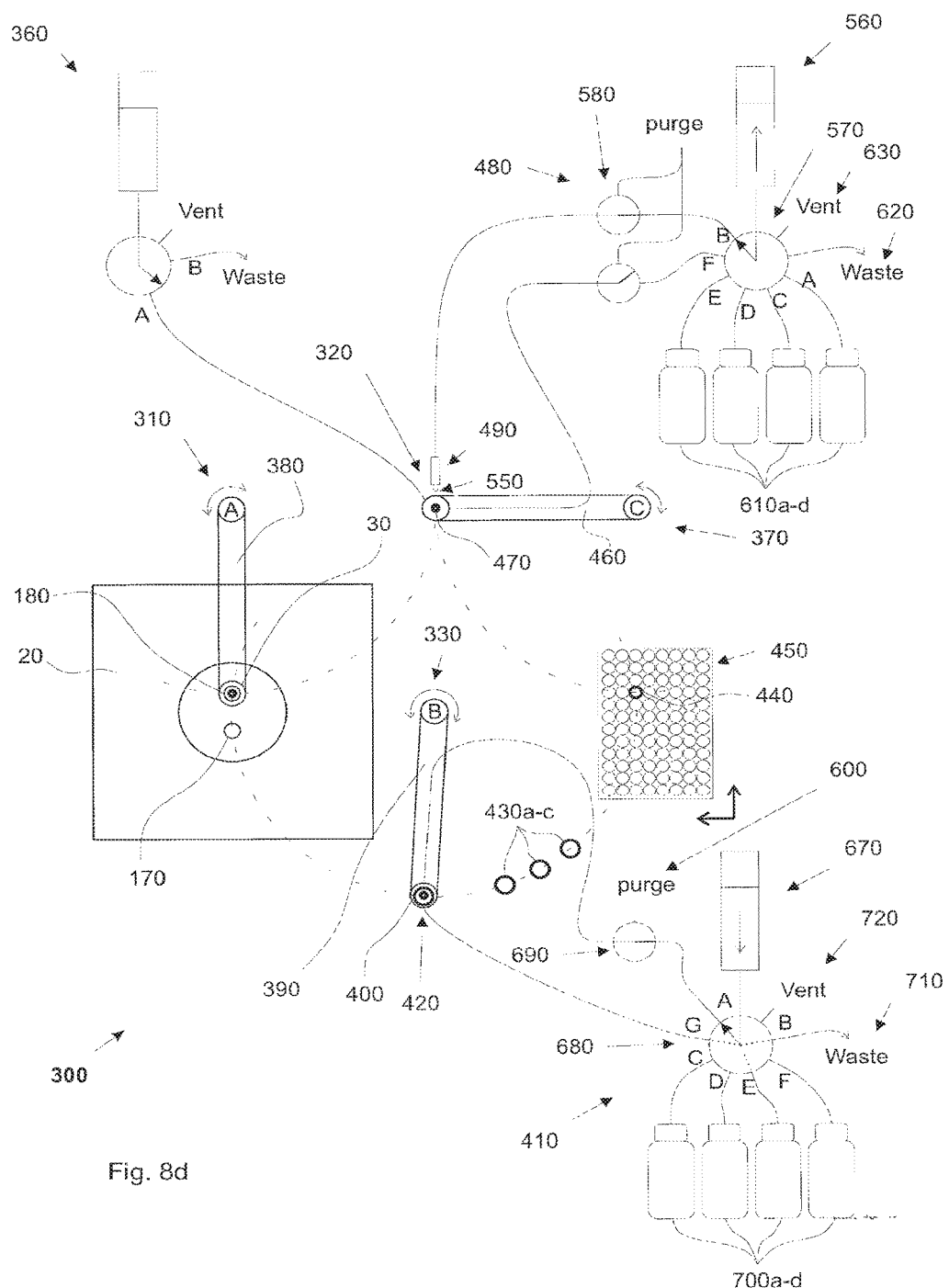

In FIG. 8c the pipette assembly 30 again is placed at the wash position with the titration needle 210 in the wash station 320 to fill the syringe 200 with titrant. As is discussed in detail with reference to FIGS. 5a-c, during filling of the syringe 200, the connection member 550 of the fill port connection unit 490 is connected to the fill port. 500 of the syringe 200, and the syringe fluidics system 480 is arranged to pull the titrant through titrant needle 210 into the syringe 200 until a small volume has passed the fill port 500, whereby the plunger 230 is lowered to close the fill port 500. By drawing the titrant into the syringe in this way, trapped air in the titrant is effectively avoided. During the state disclosed in FIG. 8b, the titrant transfer unit 370 is essentially inactive, but the cell preparation unit 330 is positioned with the cell cannula 400 in the sample cell 50 to fill the later with an exact amount of fresh sample by arranging the cell preparation control valve 680 in position A and activating the cell pump 670 to dispense the fresh sample contained in the pump reservoir into the sample cell 50.

In FIG. 8a the pipette assembly 30 is placed at the titration position with the titration needle 210 in the sample cell 50 to perform an ITC experiment. The Titration transfer unit 370 is now positioned with the titrant cannula in the wash station 320 to wash it before the next titrant transfer operation. The washing cycle may be essentially the same as for the syringe 200. During the state disclosed in FIG. 8b, the cell preparation unit 330 is essentially inactive, and shown with the cell cannula 400 in the sample preparation station 420.

Examples of Liquid Handling Sequences Includes:
Cell Wash:
a. The cell cannula 400 is inserted into the cell 40, 50, resting on the bottom.
b. The cell content is drawn through the cell cannula 400, into the cell pump 680, and dispensed out to the waste port 710.
c. Water is drawn from one of the wash liquid reservoirs 700a-d into the pump reservoir of the cell pump 680 and dispensed out to the waste port 710 to rinse the syringe.
d. A wash liquid is drawn into the pump reservoir of the cell pump 680 from one of the wash liquid reservoirs 700a-d and dispensed through the cell cannula 400 into the cell 40, 50 in the exact amount needed to fill the cell, e. The wash liquid is cycled back and forth from the pump reservoir of the cell pump 680 to the cell 40, 50 to wash the later.
f. The steps beginning at step b are repeated a predetermined number of times until the cell 40, 50.
g. The cell is emptied to waste as in step b.
h. The cell cannula 400 is moved to the sample preparation station 420 and dried with by purging gas, e.g. Nitrogen. If degassing is included in the cell load procedure, the sample preparation 420 station is cleaned before drying.

Pipette Wash:
a. The pipette 30 is placed in the wash/fill station 320 and the fill port 500 is connected.
b. The pipette plunger 230 is raised above the fill port 500 allowing liquid to flow through the syringe 200 of the pipette 30.
c. First water then air is dispensed from the syringe pump 560 into the fill port 500, through the syringe 200 and titration needle 210 into the wash/fill station 320. Simultaneously, this water is drawn in great excess from the bottom of the wash/fill station 320 through the waste outlet 350 into the waste pump 510.
d. The waste pump 510 is stopped and a precise amount of water is dispensed through the pipette 30 to fill the wash/fill station 320 to the top of the outside of the titration needle 210. The water is cycled back and forth to wash the entire syringe 200 and the titration, inside and outside.
e. Step e is repeated.
f. Step d is repeated with methanol.
g. Step c is repeated.
h. Nitrogen is purged through the fill port 500 to dry the system.
i. The pipette 30 is removed from the wash/fill station 320 to allow the titrant transfer unit 370 to load the station 320 with titrant sample.
j. The syringe pump 560 is rinsed with water to clear any methanol from the system.

Cell Load:
a. Titrant sample is drawn into the cell cannula 400 from a sample tray 450 or a sample reservoir 430a-c. It is then slowly dispensed into the cell to prevent air bubbles. Optionally, the sample is dispensed into the sample preparation station 420 to be warmed and mixed (degassed) before being transferred into the cell 50.

Pipette Load:
a. Titrant is drawn into the titrant transfer cannula 470 from a sample tray 450 and dispensed into the wash/fill station 320.
b. The pipette 30 is placed in the wash/fill station 320 and the fill port 500 is connected.
c. The plunger 230 is raised above the fill port 500 allowing liquid to flow through the pipette.
d. A precise volume of titrant is drawn up through the titration needle 210 by the syringe pump 560, overfilling the syringe 200 such that a small amount of titrant exits the fill port 500.
e. The plunger 230 is lowered below the fill port 500 leaving the titrant needle 210 and pipette syringe 200 completely filled.

Titrant Transfer Clean:
a. The titrant transfer cannula 470 is placed in the wash/fill station 320 and is rinsed with water, then rinsed with methanol and dried in much the same way that the syringe 200 of the pipette is washed and dried.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. An isothermal titration micro calorimetry (ITC) system, comprising;
    a microcalorimeter,
    a pipette assembly comprising a syringe with a fill port configured to provide fluidic contact with a cavity of the syringe and an activator configured to drive a plunger in the cavity of the syringe,
    a rotatable pipette translation unit configured to place the pipette assembly in a titration position and in a washing position,
    a rotatable cell preparation unit configured to wash a sample cell of the microcalorimeter and replace sample liquid in the sample cell when the pipette assembly is placed in another position than the position for titration, and
    a fill port connection unit comprising a connection member configured to connect to the fill port thereby enabling fluid to transfer into the cavity of the syringe.
2. The ITC system of claim 1, wherein the fluid transfers into the cavity of the syringe through the connection member when the pipette assembly is in the washing position.
3. The ITC system of claim 2, wherein the fluid comprises a washing liquid or a purge gas.
4. The ITC system of claim 2, wherein the fluid comprises titrant.
5. The ITC system of claim 1, wherein the connection member enables fluid to transfer out of the cavity of the syringe.
6. The ITC system of claim 5, wherein the fluid transfers out of the cavity of the syringe through the connection member when the pipette assembly is in the washing position.
7. The ITC system of claim 6, wherein the fluid comprises titrant.
8. The ITC system of claim 1, wherein the fill port is located at an upper portion of the syringe.
9. The ITC system of claim 8, wherein the fill port is configured to provide fluidic contact with the cavity of the syringe when the plunger is positioned above the fill port.
10. The ITC system of claim 9, wherein the activator closes the fill port by moving the plunger below the fill port.
11. The ITC system of claim 1, wherein the fill port is a bore through a wall of the syringe.

* * * * *